(12) United States Patent
Miyauchi

(10) Patent No.: US 9,346,047 B2
(45) Date of Patent: May 24, 2016

(54) ROBOT SYSTEM AND A METHOD FOR MANUFACTURING SUBJECTED-TO-OPERATION SPECIMEN

(71) Applicant: KABUSHIKI KAISHA YASKAWA DENKI, Kitakyushu-shi (JP)

(72) Inventor: Kohei Miyauchi, Kitakyushu (JP)

(73) Assignee: KABUSHIKI KAISHA YASKAWA DENKI, Kitakyushu-Shi (JP)

( * ) Notice: Subject to any disclaimer, the term of this patent is extended or adjusted under 35 U.S.C. 154(b) by 8 days.

(21) Appl. No.: 14/468,339

(22) Filed: Aug. 26, 2014

(65) Prior Publication Data

US 2015/0059149 A1 Mar. 5, 2015

(30) Foreign Application Priority Data

Aug. 29, 2013 (JP) ................................. 2013-178640

(51) Int. Cl.
| | |
|---|---|
| *G01N 35/00* | (2006.01) |
| *B01L 3/00* | (2006.01) |
| *B01L 3/02* | (2006.01) |
| *G01N 35/10* | (2006.01) |
| *B65G 59/06* | (2006.01) |

(52) U.S. Cl.
CPC .......... *B01L 3/0275* (2013.01); *G01N 35/0099* (2013.01); *G01N 35/10* (2013.01); *B65G 59/063* (2013.01); *Y10S 901/02* (2013.01); *Y10S 901/41* (2013.01); *Y10T 29/49826* (2015.01)

(58) Field of Classification Search
CPC .................................................. G01N 35/0099
See application file for complete search history.

(56) References Cited

U.S. PATENT DOCUMENTS

| | | | | |
|---|---|---|---|---|
| 3,479,795 | A * | 11/1969 | Russell | .................. B65B 5/061 53/202 |
| 5,674,047 | A * | 10/1997 | Lapeus | .................. B01L 9/543 414/795.6 |
| 6,325,114 | B1 | 12/2001 | Bevirt et al. | |
| 6,666,644 | B1 | 12/2003 | Lind et al. | |
| 6,691,748 | B1 | 2/2004 | Tajima | |
| 2006/0201810 | A1* | 9/2006 | Paschetto | .............. B01L 3/0244 204/470 |
| 2008/0090288 | A1 | 4/2008 | Hibino et al. | |
| 2008/0254545 | A1 | 10/2008 | Kitaoka | |
| 2009/0293643 | A1 | 12/2009 | Powell et al. | |
| 2012/0134896 | A1 | 5/2012 | Chiyajo et al. | |
| 2013/0125517 | A1 | 5/2013 | Gomi | |

FOREIGN PATENT DOCUMENTS

| | | |
|---|---|---|
| JP | 2006-177948 | 7/2006 |
| JP | 2008-096456 | 4/2008 |
| JP | 2008-261735 | 10/2008 |
| JP | 2013-100118 | 5/2013 |
| WO | 2012/069925 | 5/2012 |

OTHER PUBLICATIONS

Japanese Office Action for corresponding JP Application No. 2013-178640, Jun. 19, 2015.
Chinese Office Action for corresponding CN Application No. 201410295625.5, Jul. 31, 2015.
Extended European Search Report for corresponding EP Application No. 14182397.1-1553, Jan. 23, 2015.

* cited by examiner

*Primary Examiner* — P. Kathryn Wright
(74) *Attorney, Agent, or Firm* — Mori & Ward, LLP

(57) ABSTRACT

A robot system includes a robot that includes arms each including multiple joints, a controller configured to control an operation of the robot, and a tip stocker configured to supply a tip box with a pipette tip attached to and detached from a pipette with an operation of the robot. In addition, the tip stocker includes a movable member configured to be movable in accordance with an operation of the robot.

5 Claims, 15 Drawing Sheets

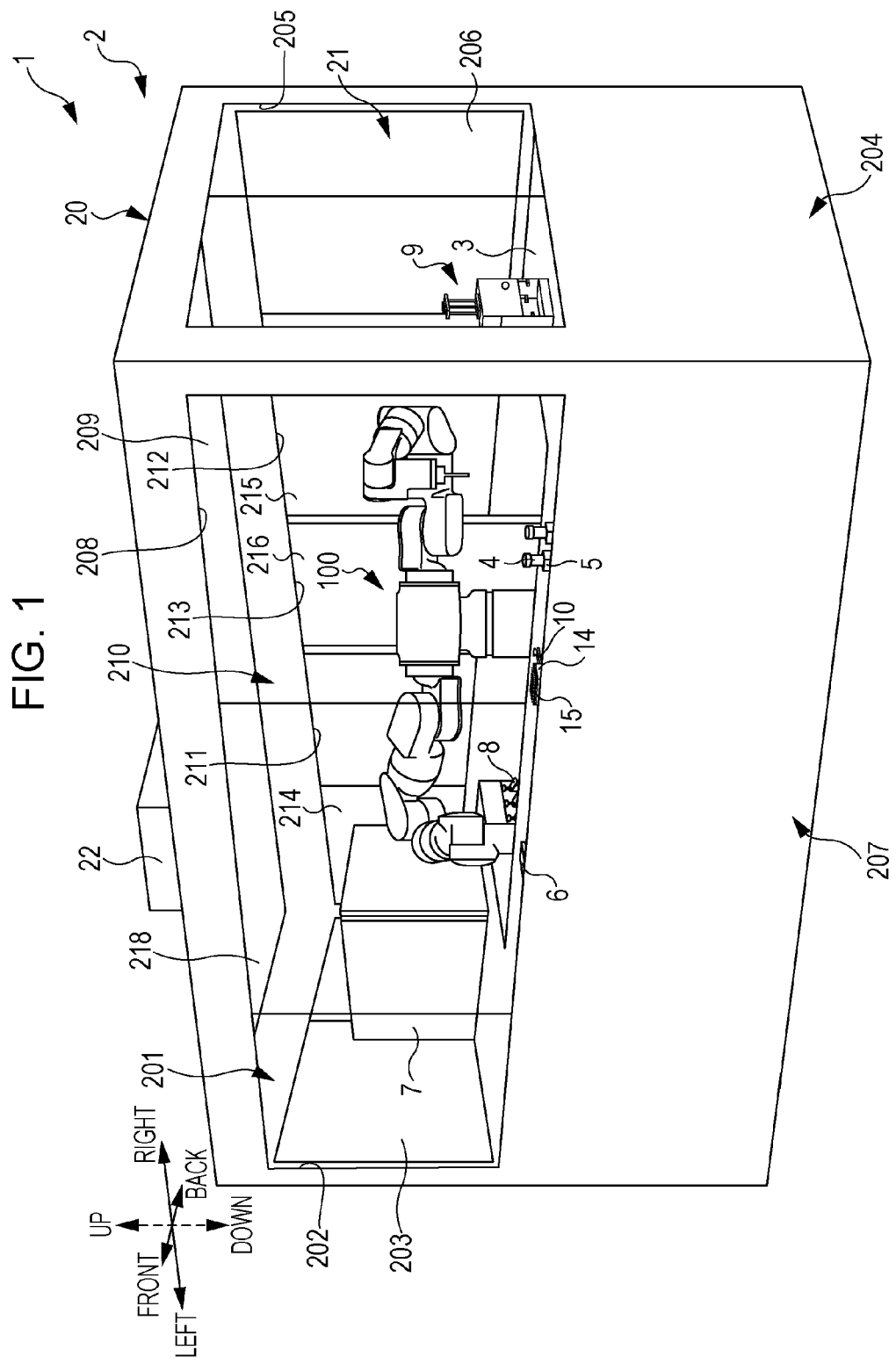

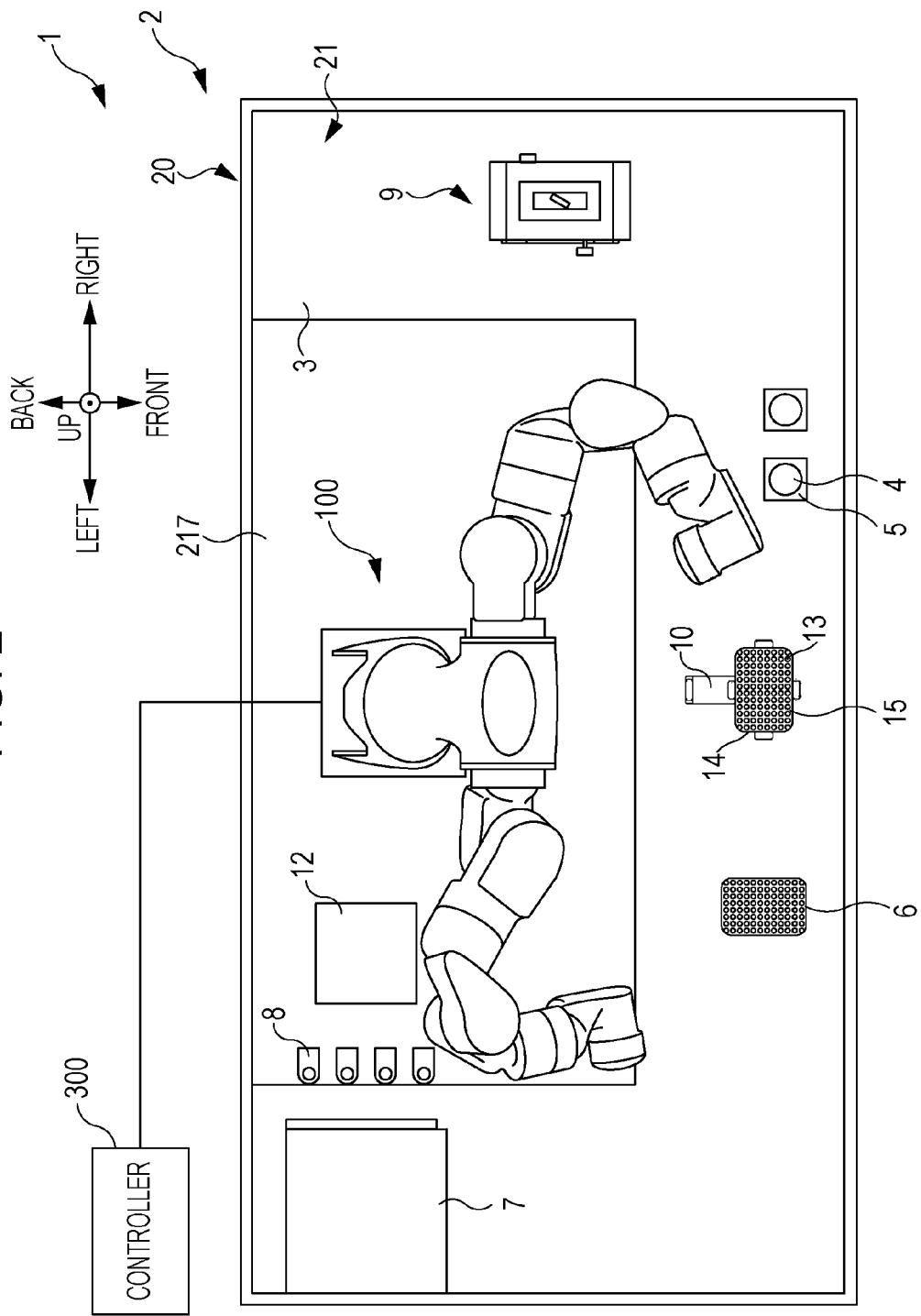

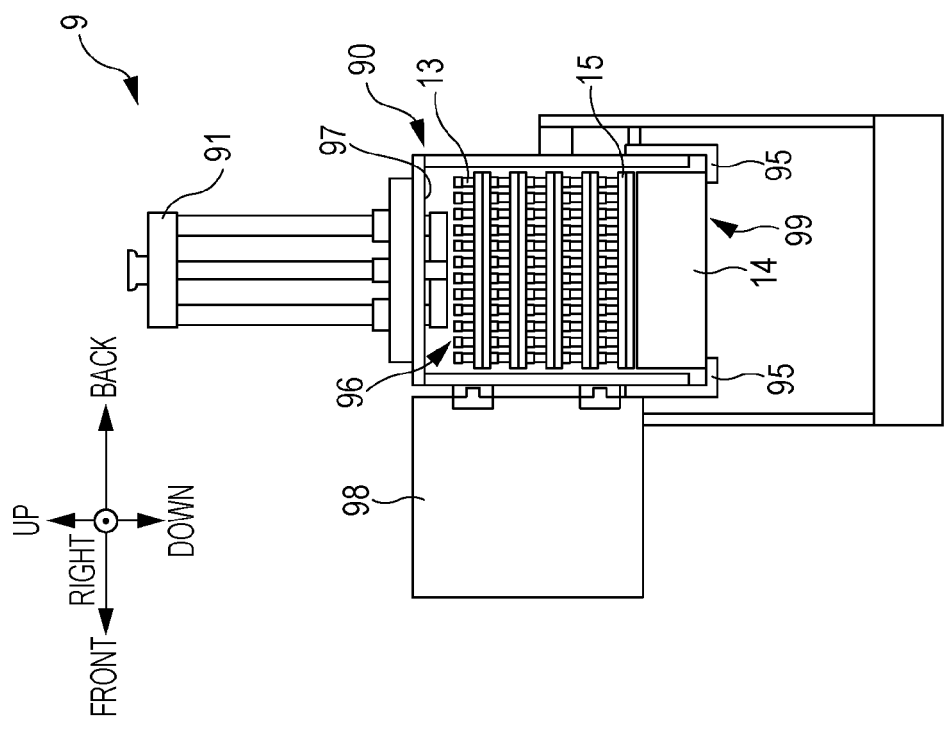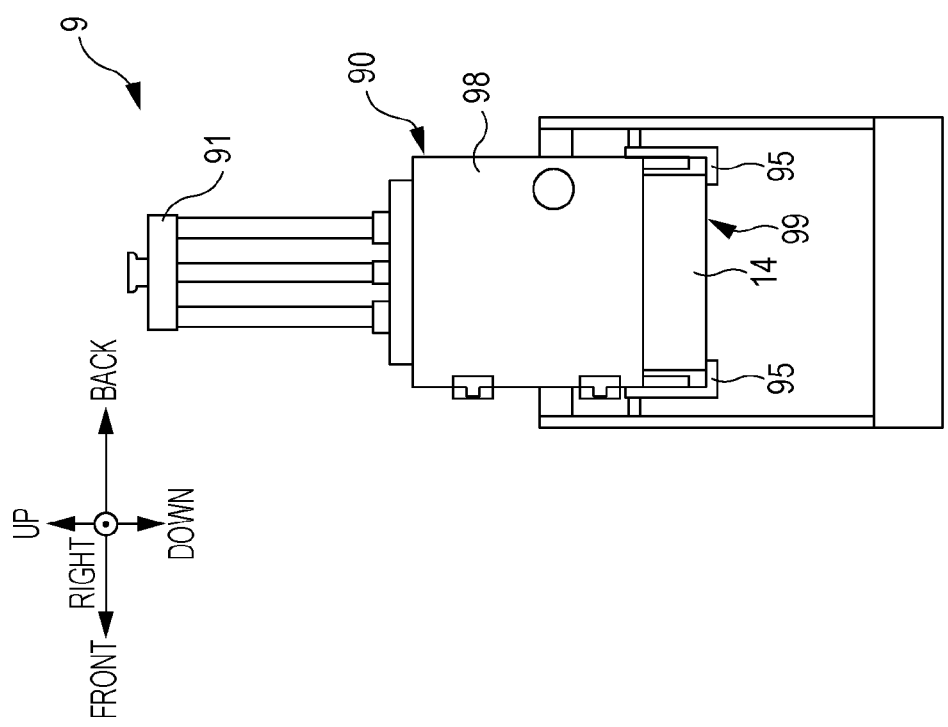

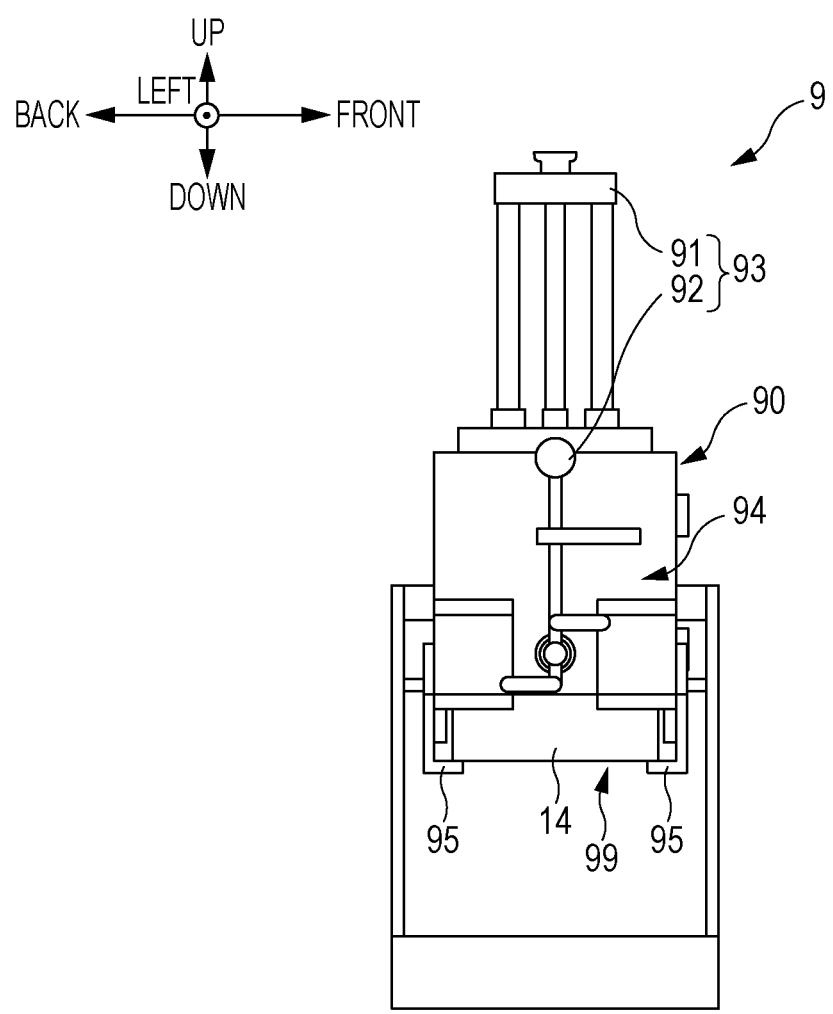

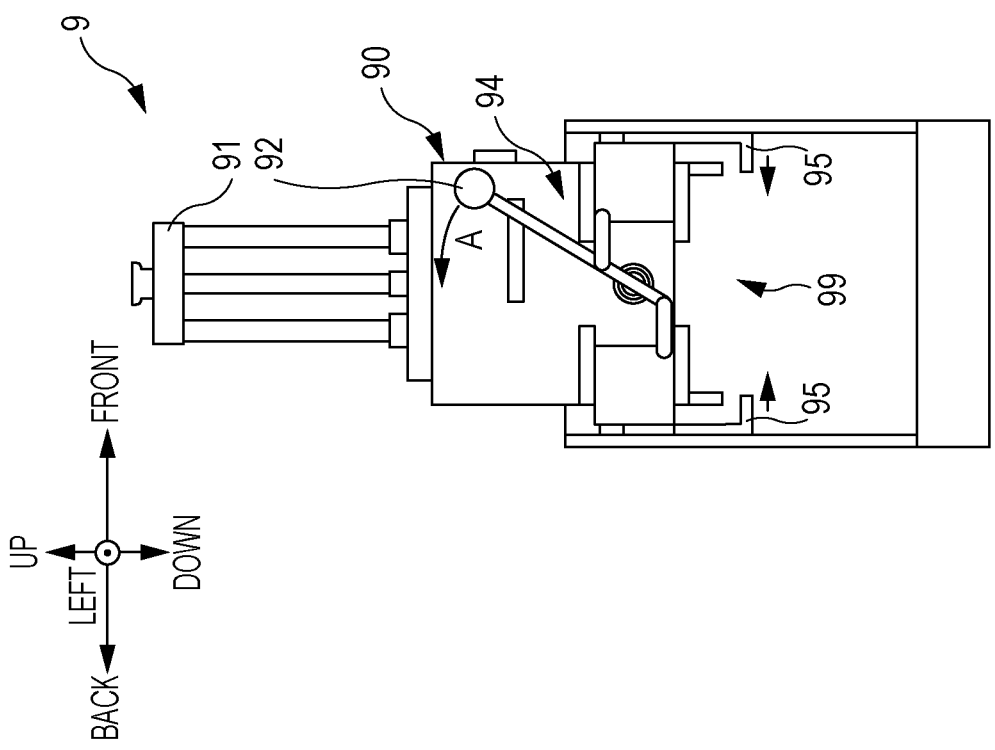
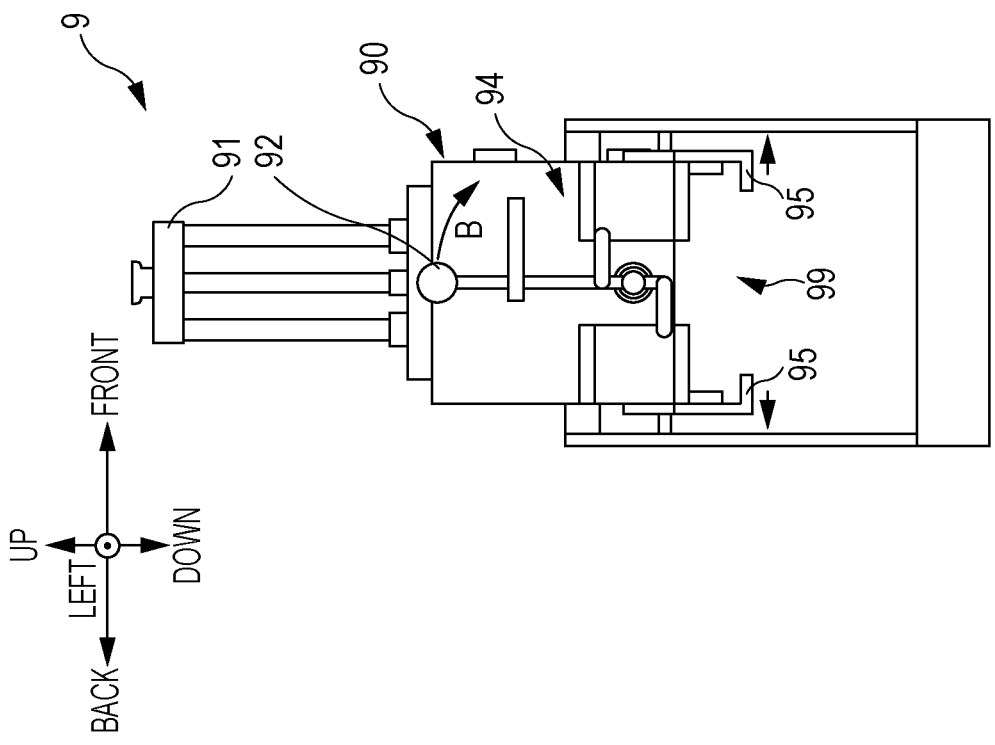

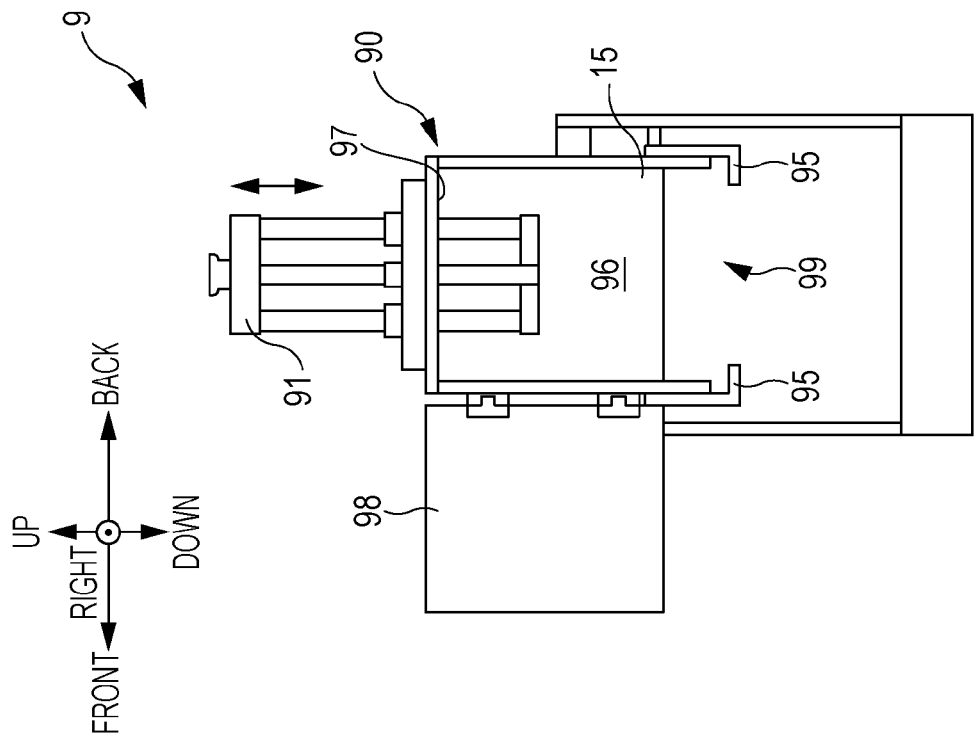
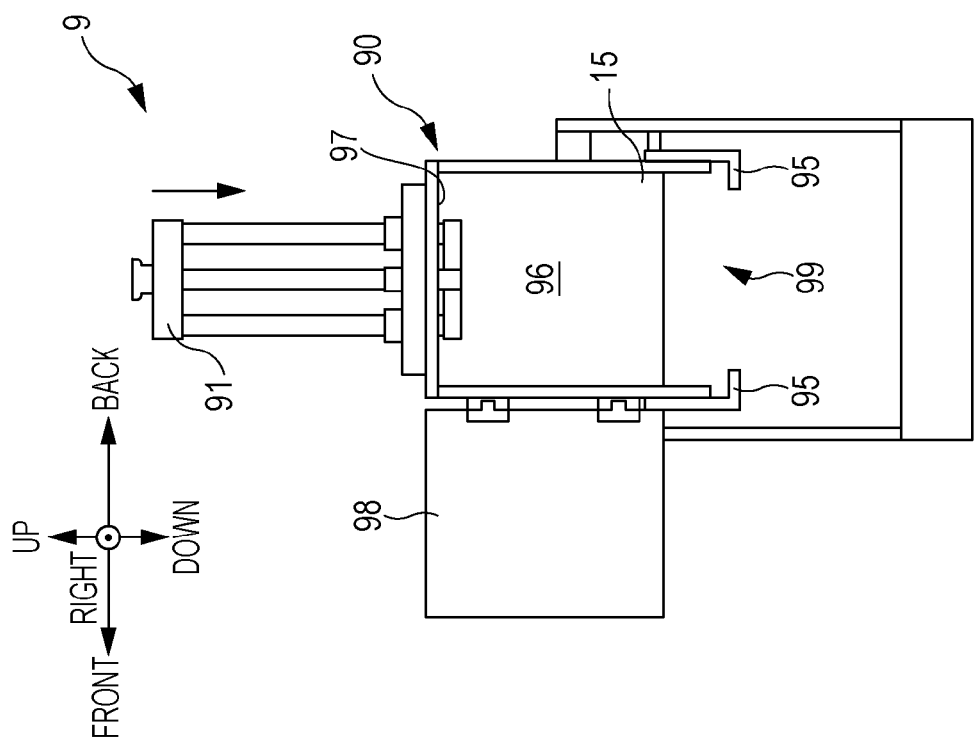

ROBOT SYSTEM AND A METHOD FOR MANUFACTURING SUBJECTED-TO-OPERATION SPECIMEN

CROSS-REFERENCE TO RELATED APPLICATIONS

The present disclosure contains subject matter related to that disclosed in Japanese Priority Patent Application JP 2013-178640 filed in the Japan Patent Office on Aug. 29, 2013, the entire contents of which are hereby incorporated by reference.

BACKGROUND

1. Field of the Invention

The embodiments disclosed herein relate to a robot system and a method for manufacturing a subjected-to-operation specimen.

2. Description of the Related Art

Japanese Unexamined Patent Application Publication No. 2006-177948 describes a dispensing apparatus for dispensing precise amounts of fluid into numerous receptacles. The dispensing apparatus includes a tray operable to carry a tip box in which multiple disposable pipette tips are arranged and a dispense block head having a face including multiple bores, each bore so sized and shaped as to receive one of the pipette tips.

SUMMARY

To address the above-described problems, according to an aspect of the disclosure, a robot system is provided that includes a robot that includes an arm including a plurality of joints; a controller configured to control an operation of the robot; and a tip feeder configured to supply a tip box with a pipette tip as a result of an operation of the robot, the pipette tip being attached to and detached from a pipette.

According to another aspect of the disclosure, a method for manufacturing a subjected-to-operation specimen using a robot that includes an arm including a plurality of joints is provided. The method includes causing the robot to operate a tip feeder to supply a tip box with a pipette tip; causing the robot to attach the pipette tip disposed on the tip box to a pipette; causing the robot to dispense the specimen using the pipette; and causing the robot to perform a predetermined operation on the specimen.

BRIEF DESCRIPTION OF THE DRAWINGS

FIG. 1 is a perspective view illustrating the schematic configuration of the entirety of a robot system according to one embodiment.

FIG. 2 is a top plan view illustrating the schematic configuration of the entirety of the robot system.

FIG. 4A is a right view of an example of the configuration of a tip stocker in the state where the right opening is closed and FIG. 4B is a right view of the example of the configuration of the tip stocker in the state where the right opening is open.

FIG. 5 is a left view illustrating an example of the configuration of the tip stocker.

FIGS. 6A and 6B illustrate forward/backward moving members, a rotatable lever, and a coupling member.

FIGS. 7A and 7B illustrate a slide lever.

DESCRIPTION OF THE EMBODIMENTS

Figure 3A:
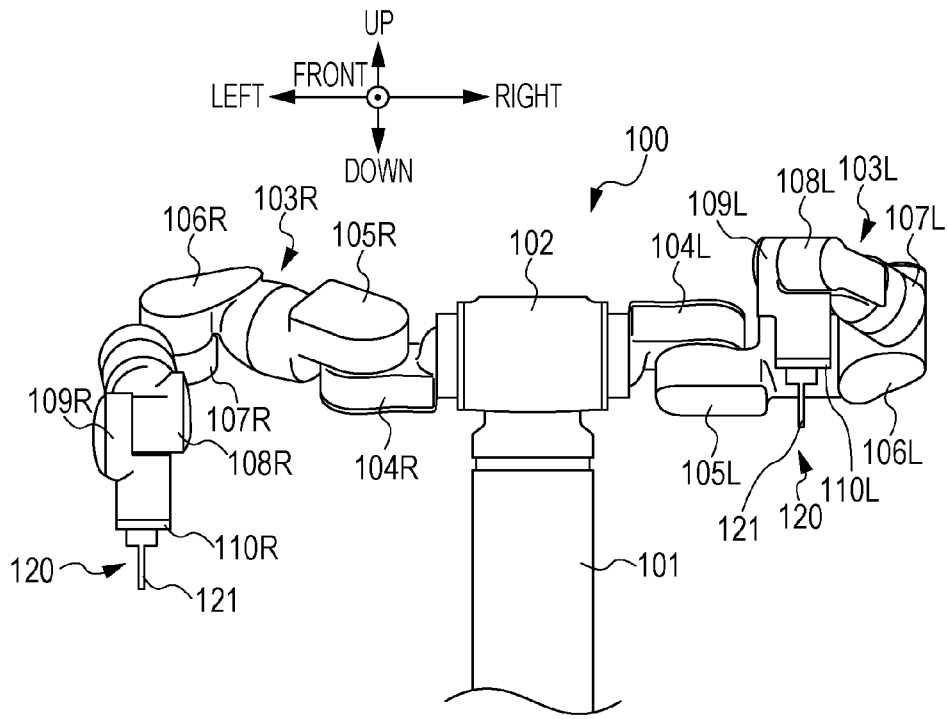
FIG. 3A is a front view of an example of the configuration of a robot and FIG. 3B is a top plan view of the example of the configuration of the robot.

Referring now to the drawings, embodiments of the disclosure are described. The terms "up", "down", "left", "right", "front", and "back" in the drawings correspond to the directions in the description including "upward", "downward", "leftward", "rightward", "frontward", and "backward". However, the positional relationship in a robot system is not limited to the concept of "up", "down", "left", "right", "front", and "back".

Schematic Configuration of Entirety of Robot System

Referring to FIGS. 1 and 2 first, the schematic configuration of the entirety of a robot system according to an embodiment will be described.

As illustrated in FIGS. 1 and 2, a robot system 1 according to this embodiment includes a robot 100, which will be described in detail below, a controller 300, and a cabinet 2 in which the robot 100 is operable.

The controller 300 is formed of a computer including components such as an arithmetic device, a memory device, and an input device. The controller 300 is intercommunicably connected to the robot 100. The controller 300 may be disposed inside the robot 100. The controller 300 controls the operation of the robot 100, which will be described below in detail.

The cabinet 2 may be any cabinet in which the robot 100 is operable. Whether or not the cabinet 2 has a function with which to adjust air flow in the internal space, a function with which to keep the internal space aseptic, or a function with which to prevent leakage of hazardous substances does not particularly matter. For convenience of illustration, however, the following describes the case where the cabinet 2 is a cabinet that has a function with which to adjust air flow in the internal space and a function with which to keep the internal space aseptic. The cabinet 2 includes a substantially rectangular-parallelepiped housing 20 and a fan 22 (an air-flow adjusting device). The housing 20 may have a shape other than a substantially rectangular-parallelepiped shape, such as a substantially cuboid shape or a substantially cylindrical shape.

An opening 202 is formed in a left wall 201 of the housing 20. A door 203 that can open and close the opening 202 is fitted in the opening 202. The door 203 is made of a material having such a translucency that the inside of the housing 20 is viewable through the door 203 from the outside of the housing 20 (for example, glass). The door 203 may be made of a material that does not have the above-described translucency. The opening 202 and the door 203 may not be provided at the left wall 201.

An opening 205 is formed in a right wall 204 of the housing 20. A door 206 (openable-closable door) that can open and close the opening 205 is fitted in the opening 205. The door 206 is made of the same material as that of the door 203. The door 206 may be made of a material that does not have the above-described translucency. The opening 205 and the door 206 may not be provided at the right wall 204.

An opening 208 is formed in a front wall 207 of the housing 20. A door 209 that can open and close the opening 208 is fitted in the opening 208. The door 209 is made of the same material as that of the door 203 and the other doors. The door 209 may be made of a material that does not have the above-described translucency. The opening 208 and the door 209 may not be provided at the front wall 207.

Openings 211, 212, and 213 are formed in a back wall 210 of the housing 20. The opening 211 is formed at a portion on the left of the back wall 210 and a door 214 that can open and close the opening 211 is fitted in the opening 211. The door 214 is made of the same material as that of the door 203 and the other doors. The door 214 may be made of a material that does not have the above-described translucency. The opening 211 and the door 214 may not be provided at the back wall 210. The opening 212 is formed at a portion on the right of the back wall 210 and a door 215 that can open and close the opening 212 is fitted in the opening 212. The door 215 is made of the same material as that of the door 203 and the other doors. The door 215 may be made of a material that does not have the above-described translucency. The opening 212 and the door 215 may not be provided at the back wall 210. The opening 213 is an entrance of the housing 20 and formed substantially throughout the back wall 210 in the vertical direction at a position between the openings 211 and 212. A door 216 that can open and close the opening 213 is fitted in the opening 213. The door 216 is made of the same material as that of the door 203 and the other doors. The door 216 may be made of a material that does not have the above-described translucency. The opening 213 and the door 216 may not be provided at the back wall 210.

The robot 100 and a worktable 3 are placed on a floor 217 inside the housing 20. Multiple pieces of equipment for operation including the pipettes 8 and a tip stocker 9 (tip feeder) are arranged within the movable range of the robot 100 inside the housing 20.

The arrangement of the worktable 3 on the floor 217 is not particularly limited. In this example, the worktable 3 is arranged on the floor 217 substantially along the left wall 201, the front wall 207, and the right wall 204.

Types of the equipment for operation arranged within the movable range of the robot 100 other than the pipettes 8 and the tip stocker 9 and the positions of the pieces of equipment for operation are not particularly limited. In this example, the equipment for operation arranged within the movable range of the robot 100 includes, besides the pipette 8 and the tip stocker 9, a tube rack 5, a tube 4, a microplate 6, an incubator 7, a pipette rack (not illustrated), a holding member 10, and a waste container 12.

The tube rack 5 is a rack for holding the tube 4 in an erect position. In this example, the tube rack 5 is disposed on the worktable 3. The tube 4 holds a specimen (such as blood, cerebrospinal fluid, urine, or part of tissue).

The microplate 6 has multiple (for example, 96) wells into which a specimen, a reagent, or the like can be injected.

The incubator 7 is a device for culturing a specimen or the like. In this example, the incubator 7 is disposed on the worktable 3. The incubator 7 can accommodate a component such as a microplate 6 holding a specimen, a reagent, or the like in its wells.

The pipette rack is a rack for holding the pipettes 8 in an erect position. In this example, the pipette rack is disposed at a side portion of the worktable 3. The pipette 8 (micropipette in this example) is a tool for aspirating and dispensing a preset amount of liquid. A disposable pipette tip 13 (see FIG. 4B and other drawings described below) is attachable to and removable from the end of the pipette 8.

The tip stocker 9 is a tool for providing the pipette tips 13 into a box-shaped tip box 14 (also see FIG. 4B and other drawings described below) with an operation of the robot 100. In this example, the tip stocker 9 can provide the pipette tips 13 to the tip box 14 by mounting flat tip pallets 15 (also see FIG. 4B and other drawings described below), on which multiple (in this example, 96) pipette tips 13 are arranged in an erect position, on the tip box 14 with the operation of the robot 100 (this operation is described in detail below). In this example, the tip stocker 9 is disposed at a position on the worktable 3 near the door 206 so that the robot 100 can operate a movable member 93, which will be described below, and so that an operator can access a tip chamber 96, described below, from the outside of the housing 20. The tip stocker 9 may not be disposed near a door provided at the housing 20, such as the door 203, other than the door 206. In addition, the tip stocker 9 may not be disposed near the door 206 or other doors provided at the housing 20 (in this case, however, an operator is to enter the housing 20 to access the tip chamber 96, described below). Multiple tip stockers 9 may be prepared in accordance with the types or the number of pipette tips 13 used.

The holding member 10 is a device used when the robot 100 holds the tip box 14.

The waste container 12 is a container for holding wastes resulting from the operation. In this example, the waste container 12 is disposed on the floor 217.

The fan 22 is disposed on a ceiling 218 of the housing 20 and adjusts air flow in the internal space 21 of the housing 20. The fan 22 may be disposed at a position other than the ceiling 218 of the housing 20 (for example, on the front wall 207). In this embodiment, the fan 22 can produce air flow flowing downward from the ceiling 218 to the floor 217, whereby the internal space 21 can be kept at a positive pressure with respect to the outside. Thus, the internal space 21 can be kept aseptic.

Configuration of Robot

Figure 3B:
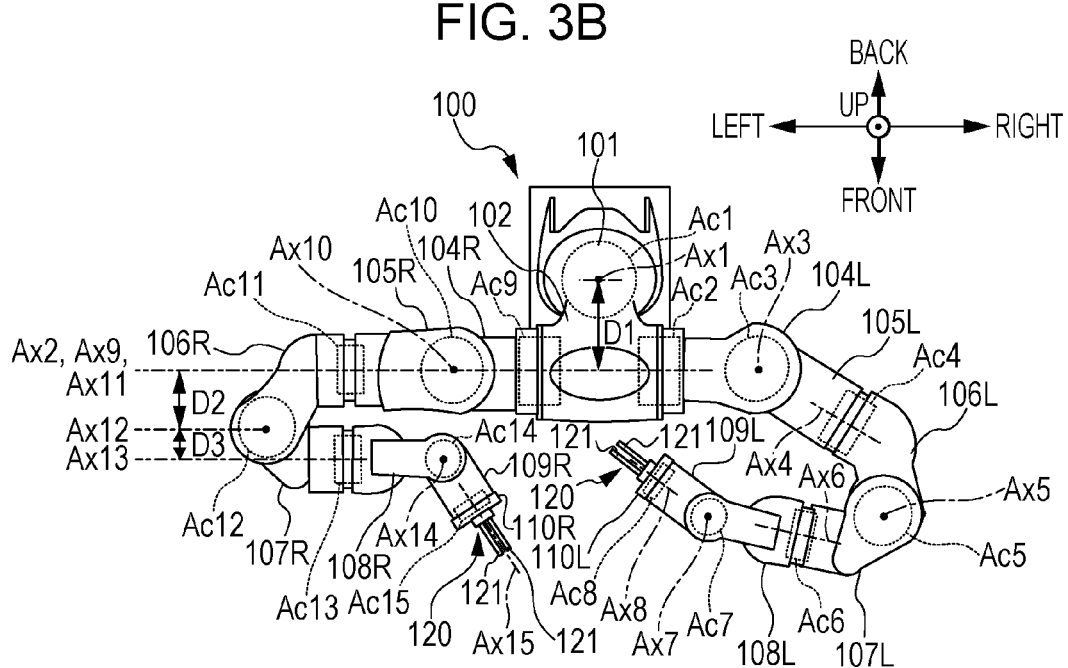

Referring now to FIGS. 3A and 3B, an example of the configuration of the robot 100 is described.

As illustrated in FIGS. 3A and 3B, the robot 100 is a so-called dual-arm robot including a base 101, a trunk 102, and two separate arms 103L and 103R.

The base 101 is secured to the surface on which the robot 100 is installed (in this example, the floor 217 in the cabinet 2) with an anchor bolt and the like. The base 101 may be secured to a surface other than the floor 217 in the cabinet 2 (for example, to the ceiling 218).

The trunk 102 is supported at the end of the base 101 so as to be capable of swiveling around a rotation axis Ax1, which is substantially perpendicular to the secured surface of the base 101. The trunk 102 is driven by an actuator Ac1, disposed at a joint between the base 101 and the trunk 102, so as to swivel around the rotation axis Ax1 with respect to the end of the base 101.

The arm 103L is rotatably supported at a portion on one side of the trunk 102. The arm 103L includes a shoulder portion 104L, a first upper-arm portion 105L, a second upper-arm portion 106L, a lower arm portion 107L, a first wrist portion 108L, a second wrist portion 109L, and a flange portion 110L.

The shoulder portion 104L is supported at a portion on one side of the trunk 102 so as to be rotatable around the rotation axis Ax2, which is substantially perpendicular to the rotation axis Ax1. The shoulder portion 104L is driven by an actuator Ac2 disposed at a joint between the trunk 102 and the shoulder portion 104L so as to rotate around the rotation axis Ax2 with respect to a portion on one side of the trunk 102.

The first upper-arm portion 105L is supported at the end of the shoulder portion 104L so as to be capable of swiveling around a rotation axis Ax3, which is substantially perpendicular to the rotation axis Ax2. The first upper-arm portion 105L is driven by an actuator Ac3, disposed at a joint between the shoulder portion 104L and the first upper-arm portion 105L, so as to swivel around the rotation axis Ax3 with respect to the end of the shoulder portion 104L.

The second upper-arm portion 106L is supported at the end of the first upper-arm portion 105L so as to be rotatable around the rotation axis Ax4, which is substantially perpendicular to the rotation axis Ax3. The second upper-arm portion 106L is driven by an actuator Ac4 disposed at a joint between the first upper-arm portion 105L and the second upper-arm portion 106L so as to rotate around the rotation axis Ax4 with respect to the end of the first upper-arm portion 105L.

The lower arm portion 107L is supported at the end of the second upper-arm portion 106L so as to be capable of swiveling around a rotation axis Ax5, which is substantially perpendicular to the rotation axis Ax4. The lower arm portion 107L is driven by an actuator Ac5, disposed at a joint between the second upper-arm portion 106L and the lower arm portion 107L, so as to swivel around the rotation axis Ax5 with respect to the end of the second upper-arm portion 106L.

The first wrist portion 108L is supported at the end of the lower arm portion 107L so as to be rotatable around a rotation axis Ax6, which is substantially perpendicular to the rotation axis Ax5. The first wrist portion 108L is driven by an actuator Ac6, disposed at a joint between the lower arm portion 107L and the first wrist portion 108L, so as to rotate around the rotation axis Ax6 with respect to the end of the lower arm portion 107L.

The second wrist portion 109L is supported at the end of the first wrist portion 108L so as to be capable of swiveling around a rotation axis Ax7, which is substantially perpendicular to the rotation axis Ax6. The second wrist portion 109L is driven by an actuator Ac7, disposed at a joint between the first wrist portion 108L and the second wrist portion 109L, so as to swivel around the rotation axis Ax7 with respect to the end of the first wrist portion 108L.

The flange portion 110L is supported at the end of the second wrist portion 109L so as to be rotatable around a rotation axis Ax8, which is substantially perpendicular to the rotation axis Ax7. The flange portion 110L is driven by an actuator Ac8 disposed at a joint between the second wrist portion 109L and the flange portion 110L so as to rotate around the rotation axis Ax8 with respect to the end of the second wrist portion 109L. In addition, a hand 120 is attached to the end of the flange portion 110L.

The hand 120 attached to the end of the flange portion 110L rotates around the rotation axis Ax8 concurrently with rotation of the flange portion 110L around the rotation axis Ax8. The hand 120 includes a pair of claw members 121 and 121 movable in directions toward and away from each other. Using the claw members 121 and 121, the hand 120 is capable of holding components, such as the tube 4, the microplate 6, the pipette 8, the holding member 10, or the tip box 14 or operating components, such as the incubator 7, the pipette 8, the tip stocker 9, or an agitator 11.

On the other hand, the arm 103R has such a configuration that the arms 103L and 103R have left-right symmetry. The arm 103R is rotatably supported at a portion on the other side of the trunk 102. The arm 103R includes a shoulder portion 104R, a first upper-arm portion 105R, a second upper-arm portion 106R, a lower arm portion 107R, a first wrist portion 108R, a second wrist portion 109R, and a flange portion 110R.

The shoulder portion 104R is supported at a portion on the other side of the trunk 102 so as to be rotatable around the rotation axis Ax9, which is substantially perpendicular to the rotation axis Ax1. The shoulder portion 104R is driven by an actuator Ac9 disposed at a joint between the trunk 102 and the shoulder portion 104R so as to rotate around the rotation axis Ax9 with respect to a portion on the other side of the trunk 102.

The first upper-arm portion 105R is supported at the end of the shoulder portion 104R so as to be capable of swiveling around a rotation axis Ax10, which is substantially perpendicular to the rotation axis Ax9. The first upper-arm portion 105R is driven by an actuator Ac10, disposed at a joint between the shoulder portion 104R and the first upper-arm portion 105R, so as to swivel around the rotation axis Ax10 with respect to the end of the shoulder portion 104R.

The second upper-arm portion 106R is supported at the end of the first upper-arm portion 105R so as to be rotatable around the rotation axis Ax11, which is substantially perpendicular to the rotation axis Ax10. The second upper-arm portion 106R is driven by an actuator Ac11 disposed at a joint between the first upper-arm portion 105R and the second upper-arm portion 106R so as to rotate around the rotation axis Ax11 with respect to the end of the first upper-arm portion 105R.

The lower arm portion 107R is supported at the end of the second upper-arm portion 106R so as to be capable of swiveling around a rotation axis Ax12, which is substantially perpendicular to the rotation axis Ax11. The lower arm portion 107R is driven by an actuator Ac12, disposed at a joint between the second upper-arm portion 106R and the lower arm portion 107R, so as to swivel around the rotation axis Ax12 with respect to the end of the second upper-arm portion 106R.

The first wrist portion 108R is supported at the end of the lower arm portion 107R so as to be rotatable around a rotation axis Ax13, which is substantially perpendicular to the rotation axis Ax12. The first wrist portion 108R is driven by an actuator Ac13, disposed at a joint between the lower arm portion 107R and the first wrist portion 108R, so as to rotate around the rotation axis Ax13 with respect to the end of the lower arm portion 107R.

The second wrist portion 109R is supported at the end of the first wrist portion 108R so as to be capable of swiveling around a rotation axis Ax14, which is substantially perpendicular to the rotation axis Ax13. The second wrist portion 109R is driven by an actuator Ac14, disposed at a joint between the first wrist portion 108R and the second wrist portion 109R, so as to swivel around the rotation axis Ax14 with respect to the end of the first wrist portion 108R.

The flange portion 110R is supported at the end of the second wrist portion 109R so as to be rotatable around a rotation axis Ax15, which is substantially perpendicular to the rotation axis Ax14. The flange portion 110R is driven by an actuator Ac15 disposed at a joint between the second wrist portion 109R and the flange portion 110R so as to rotate around the rotation axis Ax15 with respect to the end of the second wrist portion 109R. In addition, a hand 120 is attached to the end of the flange portion 110R.

The hand 120 attached to the end of the flange portion 110R rotates around the rotation axis Ax15 concurrently with rotation of the flange portion 110R around the rotation axis Ax15. The hand 120 includes a pair of claw members 121 and 121 movable toward and away from each other. Using the claw members 121 and 121, the hand 120 is capable of holding components, such as the tube 4, the microplate 6, the pipette 8, the holding member 10, or the tip box 14 and capable of operating components, such as the incubator 7, the pipette 8, the tip stocker 9, or the agitator 11.

Here, as illustrated in FIG. 3B, the trunk 102 is disposed so as to protrude from the base 101 in such a manner that the rotation axes Ax2, Ax9, and Ax11 are offset from the rotation axis Ax1 by a distance D1 in a direction substantially perpendicular to the secured surface of the base 101. Thus, a space under the shoulder portions 104L and 104R is usable as a working space and the reachable range of the arms 103L and 103R is expanded by rotating the trunk 102 around the rotation axis Ax1.

Here, the shape of the second upper-arm portion 106R is determined so that the rotation axis Ax12 is offset from the rotation axis Ax11 by a distance D2 when viewed in a plan and the shape of the lower arm portion 107R is determined so that the rotation axis Ax13 is offset from the rotation axis Ax12 by a distance D3 when viewed in a plan. When the robot 100 takes such a position that the rotation axis Ax11 and the rotation axis Ax13 are substantially parallel to each other, the distance by which the rotation axis Ax13 is offset from the rotation axis Ax11 is D2+D3. Thus, when the joint between the second upper-arm portion 106R and the lower arm portion 107R, which corresponds to the human "elbow", is bent, a large clearance can be left between the first and second upper-arm portions 105R and 106R, corresponding to the human "upper arm", and the lower arm portion 107R, corresponding to the human "lower arm". Thus, the arm 103R can be operated more flexibly even when the hand 120 attached to the end of the flange portion 110R is brought close to the trunk 102.

Although not illustrated in FIG. 3B, also in the arm 103L, the shape of the second upper-arm portion 106L is determined so that the rotation axis Ax5 is offset from the rotation axis Ax4 by a distance D2 when viewed in a plan and the shape of the lower arm portion 107L is determined so that the rotation axis Ax6 is offset from the rotation axis Ax5 by a distance D3 when viewed in a plan. When the robot 100 takes such a position that the rotation axis Ax4 and the rotation axis Ax6 are substantially parallel to each other, the distance by which the rotation axis Ax6 is offset from the rotation axis Ax4 is D2+D3.

Each of the actuators Ac1 to Ac15 is composed of a servomotor including, for example, a speed reducer. Information on the rotation angle positions of the actuators Ac1 to Ac15 is output to the controller 300 per predetermined calculation cycle in the form of signals from rotation-angle-position sensors (not illustrated) installed in the actuators Ac1 to Ac15.

In the above description, for the purpose of distinction, rotation around a rotation axis extending in the longitudinal direction of the arms 103L and 103R (or in the direction in which the arms 103L and 103R extend) is referred to as "rotation" while rotation around a rotation axis that is substantially perpendicular to the longitudinal direction of the arms 103L and 103R is referred to as "swivel".

The term "perpendicular" in the above description is not used in the strict sense and allows for actually developed tolerance or error. The term "perpendicular" in the above description does not mean that imaginary axes cross each other. As long as the directions of the imaginary axes cross each other, the case where the imaginary axes are in skew positions is also regarded as the case where the axes are perpendicular to each other.

Configuration of Tip Stocker

The configuration of the tip stocker 9 is not particularly limited and may have any configuration in which the tip stocker 9 can supply the pipette tips 13 to the tip box 14 as a result of an operation of the robot 100. An example of the configuration of the tip stocker 9 is described below with reference to FIGS. 4A, 4B, 5, 6A, 6B, 7A, and 7B.

As illustrated in FIGS. 4A, 4B, 5, 6A, 6B, 7A, and 7B, the tip stocker 9 includes a substantially cuboid housing 90, forward/backward moving members 95, a movable member 93, and a linkage 94. Here, the housing 90 may have a shape other than a substantially cuboid shape (for example, a substantially rectangular parallelepiped shape or a substantially cylindrical shape).

An opening 97 provided for accessing the tip chamber 96, which is the internal space of the housing 90, is formed on the right side of the housing 90. A door 98 that can open and close the opening 97 is fitted in the opening 97. Operators can access the tip chamber 96 by opening the door 206 of the cabinet 2 from the outside of the cabinet 2 and then opening the door 98 of the tip stocker 9.

The tip chamber 96 is a chamber for housing the tip pallet 15 on which multiple pipette tips 13 are arranged in an erect position. In this example, the tip chamber 96 can accommodate multiple tip pallets 15 stacked one on top of the other, on each of which multiple pipette tips 13 are mounted in an erect position. An operator places, in the tip chamber 96 in advance, a tip box 14 on which multiple (five, in this example) tip pallets 15 stacked one on top of the other are mounted, multiple pipette tips 13 being mounted in an erect position on each of the tip pallets 15. Here, an operator may place multiple empty tip pallets 15 in the tip chamber 96 in advance.

Figure 8A:
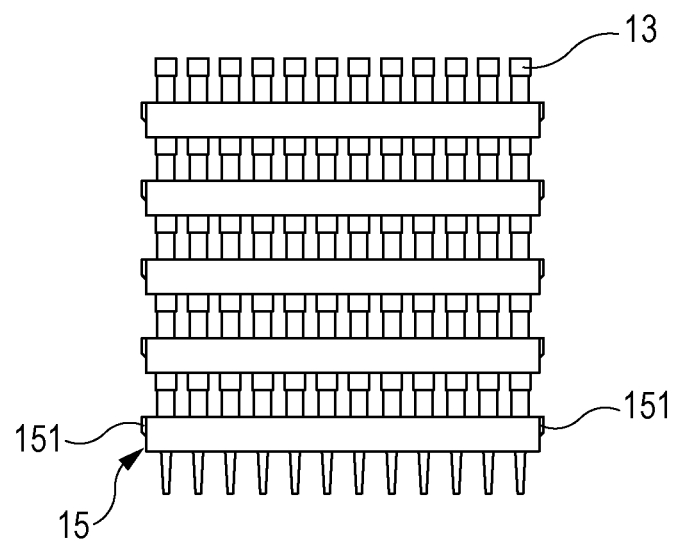
FIG. 8A is a side view of multiple layers of tip pallets and FIG. 8B is a side view of a tip box on which a tip pallet is mounted.
Figure 8B:
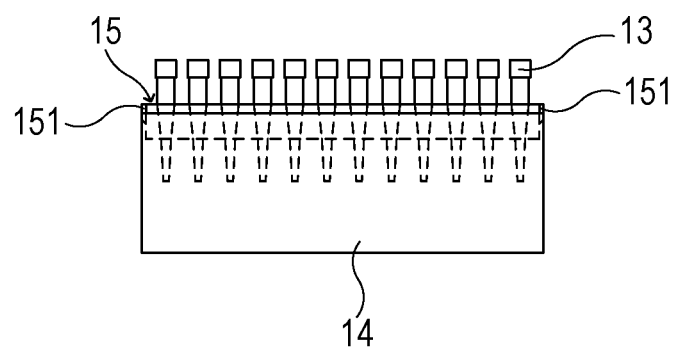

As illustrated in FIG. 8A, hooks 151 and 151 are provided on both sides of each of the multiple tip pallets 15. The hooks 151 and 151 are capable of being engaged with edge portions on both sides of the tip box 14. As illustrated in FIG. 8B, the tip pallet 15 is mounted on the tip box 14 while the hooks 151 and 151 are engaged with the edge portions of the tip box 14.

As illustrated in FIGS. 4A, 4B, 5, 6A, 6B, 7A, and 7B, an opening 99 into which the tip pallets 15 housed in the tip chamber 96 are pushed out is formed at a lower portion of the housing 90.

The forward/backward moving members 95 are members that are movable into and out of the opening 99 in directions such as to open and close the opening 99. The forward/backward moving members 95 are not particularly limited and may be any members that are movable into and out of the opening 99 in directions such as to open and close the opening 99. In this example, at least one pair of forward/backward moving members 95 and 95 are provided in a lower portion of the housing 90. The forward/backward moving members 95 and 95 are movable into and out of the opening 99 in directions such as to open and close the opening 99 by moving toward and away from each other. The forward/backward moving members 95 and 95 are used to hold and release the tip box 14 housed in the tip chamber 96.

The movable member 93 is a member that is movable in accordance with the operation of the robot 100. In this example, the movable member 93 includes a rotatable lever 92 and a slide lever 91.

The rotatable lever 92 is a lever that can move, with a rotational operation, the forward/backward moving members 95 and 95 into and out of the opening 99 in directions such as to open and close the opening 99. The rotatable lever 92 is not particularly limited and may be any lever that can move, with a rotational operation, the forward/backward moving members 95 and 95 into and out of the opening 99 in directions such as to open and close the opening 99. In this example, the rotatable lever 92 is disposed on the right side of the housing 90 and connected to the forward/backward moving members 95 and 95 with the coupling member 94 therebetween. The rotatable lever 92 can move, with a rotational operation, the forward/backward moving members 95 and 95, coupled with the coupling member 94, into and out of the opening 99 toward and away from each other by driving the coupling member 94.

For example, when the rotatable lever 92 taking the position illustrated in FIG. 6B is rotated in the direction of arrow A to the position illustrated in FIG. 6A in which the forward/backward moving members 95 and 95 have been moved into the opening 99 in directions toward each other (in directions such as to close the opening 99), the opening 99 is narrowed, so that the tip box 14 housed in the tip chamber 96 can be held in the tip chamber 96. On the other hand, when the rotatable lever 92 taking the position illustrated in FIG. 6A is rotated in the direction of arrow B to the position illustrated in FIG. 6B in which the forward/backward moving members 95 and 95 have been moved out of the opening 99 in directions away from each other (in directions such as to open the opening 99), the opening 99 is widened, so that the tip box 14 housed in the tip chamber 96 can be dropped out of the tip chamber 96. Here, even after the tip box 14 housed in the tip chamber 96 is dropped out of the tip chamber 96, the tip pallet 15 housed in the tip chamber 96 is designed to be left in the tip chamber 96.

The slide lever 91 is a lever slidable into and out of the tip chamber 96. The slide lever 91 is not particularly limited and may be any lever that is slidable into and out of the tip chamber 96. In this example, the slide lever 91 is vertically slidable into and out of the tip chamber 96. When the slide lever 91 is pushed downward from above so as to slide into the tip chamber 96, the tip pallet 15 housed in the tip chamber 96 can be pushed out of the tip chamber 96.

Functional Configuration of Controller

Figure 9:
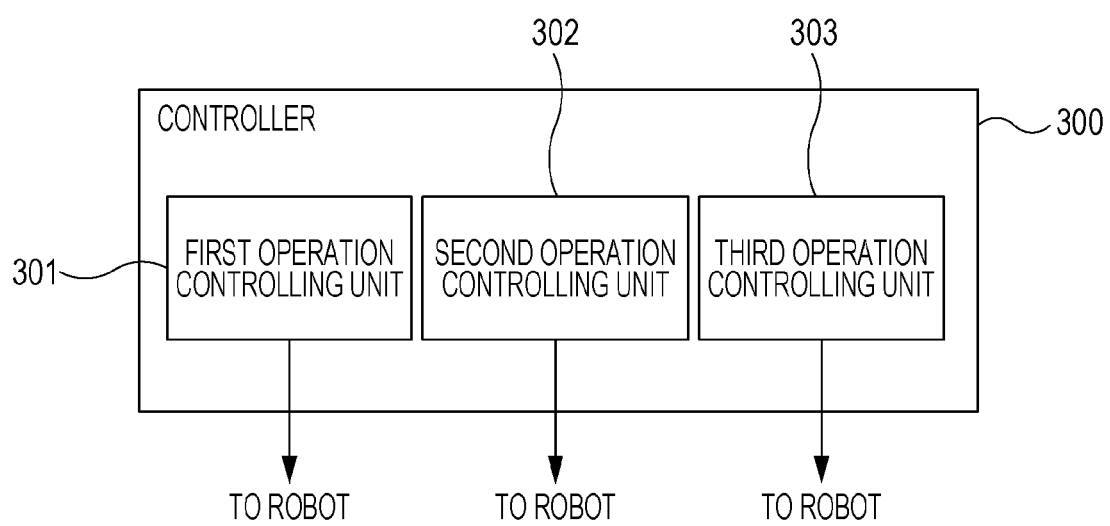
FIG. 9 is a block diagram of an example of a functional configuration of a controller.

Referring now to FIG. 9, an example of the functional configuration of the controller 300 is described.

As illustrated in FIG. 9, the controller 300 includes a first operation controlling unit 301, a second operation controlling unit 302, and a third operation controlling unit 303.

The first operation controlling unit 301 controls the operation of the robot 100 in such a manner that the slide lever 91 slides into and out of the tip chamber 96. In this example, the first operation controlling unit 301 controls the operation of the robot 100 in such a manner that the slide lever 91 slides downward into the tip chamber 96 so that multiple tip pallets 15 housed in the tip chamber 96 are pushed out of the tip chamber 96 one by one. In the case where the tip chamber 96 is emptied as a result of all the tip pallets 15 housed in the tip chamber 96 being pushed out of the tip chamber 96, the first operation controlling unit 301 controls the operation of the robot 100 in such a manner that the slide lever 91 slides upward out of the tip chamber 96.

The second operation controlling unit 302 controls the operation of the robot 100 so that the robot 100 rotates the rotatable lever 92. In this example, the second operation controlling unit 302 controls the operation of the robot 100 so that, when the tip box 14 on which multiple tip pallets 15 are mounted is placed in the tip chamber 96, the robot 100 rotates the rotatable lever 92 in the direction of arrow A (moves the forward/backward moving members 95 and 95 into the opening 99 toward each other). The second operation controlling unit 302 controls the operation of the robot 100 so that, when a dispensing process is started, the robot 100 rotates the rotatable lever 92 in the direction of arrow B (moves the forward/backward moving members 95 and 95 out of the opening 99 away from each other).

The third operation controlling unit 303 controls the operation of the robot 100 so that the hand 120 attached to the arm 103R (or the arm 103L) turns the tip box 14 held with the claw members 121 and 121 upside down (or tilts the tip box 14).

Example of Operation Flow

Figure 10:
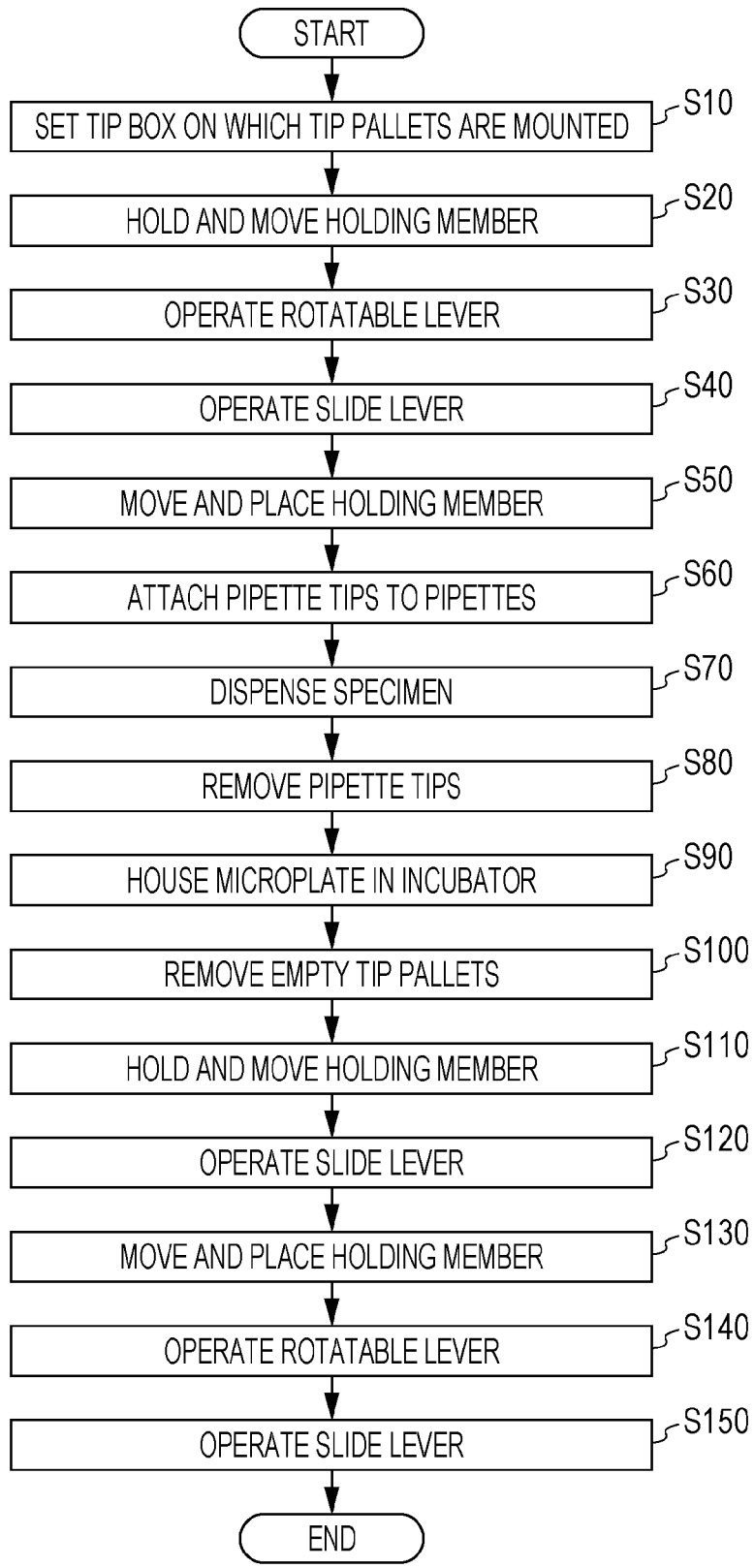
FIG. 10 is a flowchart illustrating an example of an operation flow.

Referring now to FIG. 10, an example of an operation flow including multiple steps in a method for manufacturing a subjected-to-operation specimen using the robot 100 is described.

In FIG. 10, when the operation is started, the tip stocker 9 is in the state where the forward/backward moving members 95 and 95 have been moved into the opening 99 toward each other as a result of rotation of the rotatable lever 92 in the direction of arrow A and the slide lever 91 is out of the tip chamber 96 as a result of sliding upward (in the state illustrated in FIG. 6A).

In Step S10, an operator opens the door 206 of the cabinet 2 and then opens the door 98 of the tip stocker 9 from the outside of the cabinet 2. Subsequently, the operator accesses the tip chamber 96 of the tip stocker 9 and places the tip box 14, on which multiple tip pallets 15 are mounted, in the tip chamber 96 to cause the forward/backward moving members 95 and 95 to hold the tip box 14. Then, the operator closes the door 98 and the door 206 from the outside of the cabinet 2.

In Step S20, the controller 300 controls the operation of the robot 100 so that the robot 100 holds the holding member 10 placed on the worktable 3 using the claw members 121 and 121 of the hand 120 attached to the arm 103R (or the arm 103L). The controller 300 then controls the operation of the robot 100 so that the robot 100 moves the held holding member 10 to a position immediately below the tip box 14 housed in the tip chamber 96 (or immediately below the opening 99) (see FIG. 11).

Figure 11:
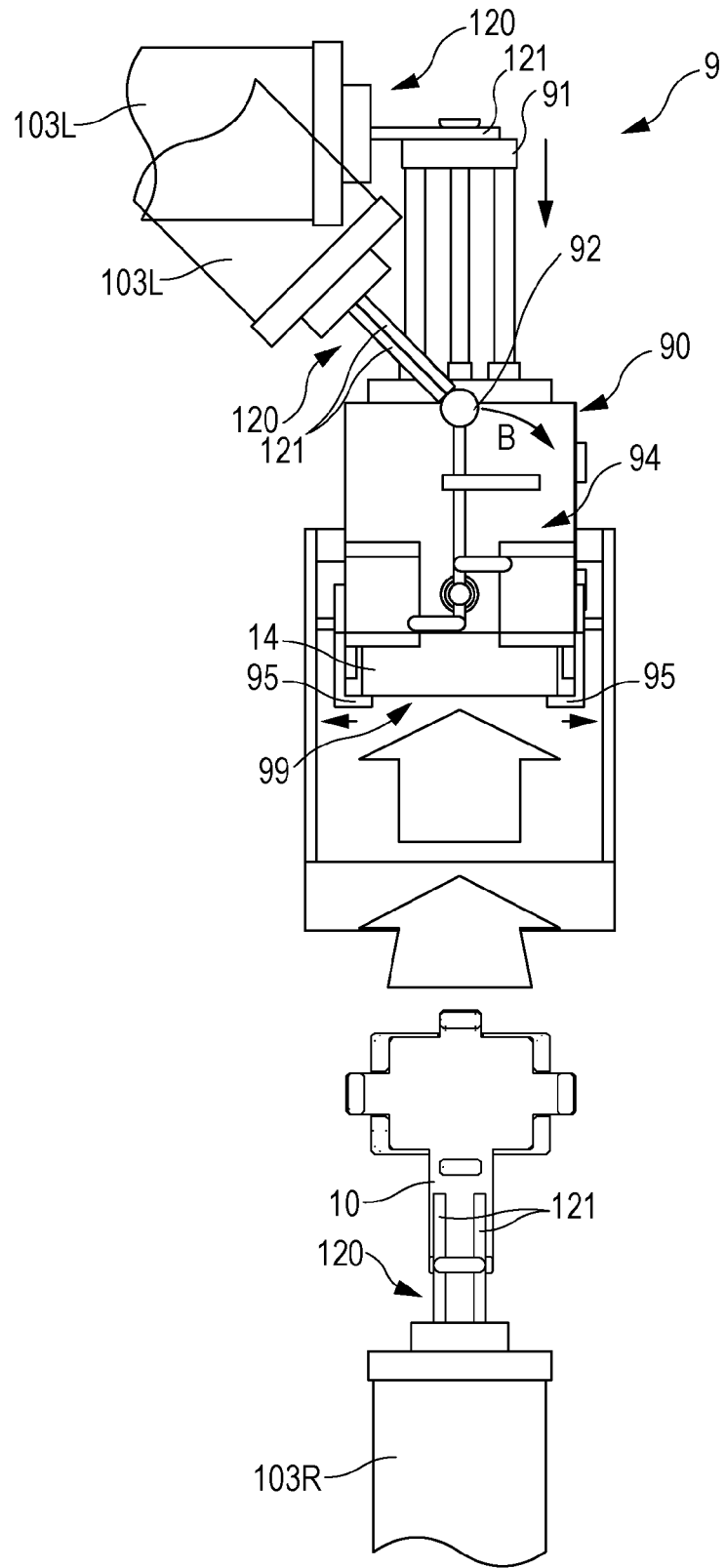
FIG. 11 illustrates an operation of a robot.
Figure 12:
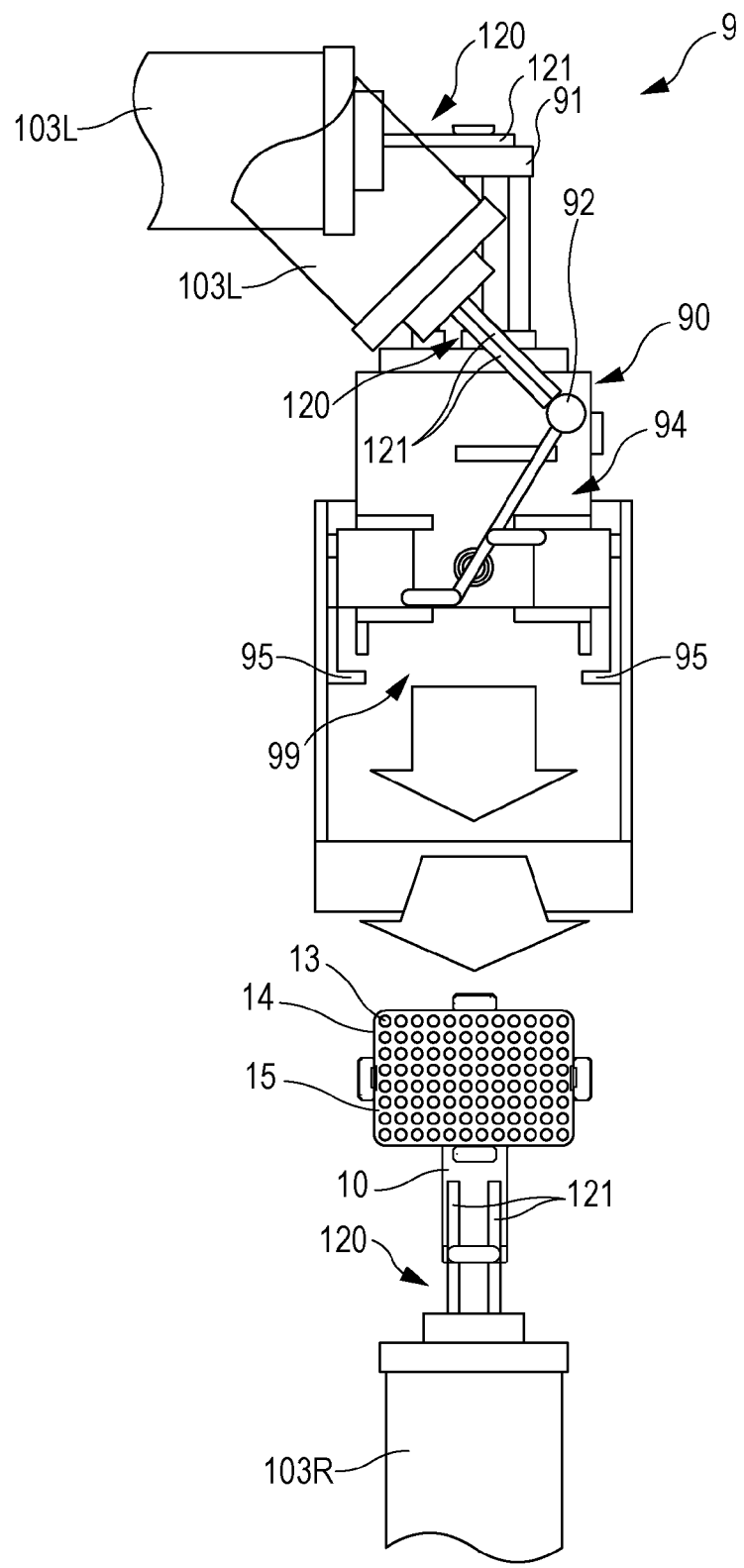
FIG. 12 illustrates an operation of a robot.

In Step S30, the second operation controlling unit 302 of the controller 300 controls the operation of the robot 100 so that the robot 100 rotates the rotatable lever 92 in the direction of arrow B using the claw members 121 of the hand 120 attached to the arm 103L (or the arm 103R) (see FIG. 11 and FIG. 12). The rotation of the rotatable lever 92 in the direction of arrow B moves the forward/backward moving members 95 and 95 out of the opening 99 away from each other and opens the opening 99, whereby the tip box 14 is dropped out of the tip chamber 96 and then held by the held holding member 10.

In Step S40, the first operation controlling unit 301 of the controller 300 controls the operation of the robot 100 so that the robot 100 slides the slide lever 91 into the tip chamber 96 downward by a predetermined distance so that only one of the tip pallets 15 housed in the tip chamber 96 is pushed out of the tip chamber 96 by the claw members 121 of the hand 120 attached to the arm 103L (or the arm 103R) (see FIG. 11 and FIG. 12). As a result of sliding the slide lever 91 into the tip chamber 96 downward by a predetermined distance, the tip pallets 15 housed in the tip chamber 96 is pushed from above by a predetermined distance and only one of the tip pallets 15 is pushed out of the tip chamber 96. Then, the tip pallet 15 thus pushed out is mounted on the held tip box 14.

In Step S50, the controller 300 controls the operation of the robot 100 so that the robot 100 moves the holding member 10, held by the hand 120 attached to the arm 103R using the claw members 121 and 121 and holding the tip box 14 on which the tip pallet 15 is mounted, from the position immediately below the opening 99 onto the worktable 3 and places the holding member 10 on the worktable 3 (see FIG. 12).

In Step S60, the controller 300 controls the operation of the robot 100 so that the robot 100 holds the pipette 8 using the claw members 121 and 121 of the hand 120 attached to the arm 103R (or the arm 103L). Then, the controller 300 controls the operation of the robot 100 so that the robot 100 attaches, to the end of the held pipette 8, one of the pipette tips 13 arranged on the tip pallet 15 on the tip box 14 held by the holding member 10 thus placed.

In Step S70, the controller 300 controls the operation of the robot 100 so that the robot 100 dispenses the specimen in the tube 4 to the wells of the microplate 6 using the held pipette 8.

At predetermined time (for example, when dispensing to all the wells is finished or every time when dispensing to one well is finished), the controller 300 controls the operation of the robot 100 in Step S80 so that the robot 100 removes the used pipette tip 13 attached to the end of the held pipette 8. Thus, the used pipette tip 13 thus removed is thrown into the waste container 12.

In Step S90, the controller 300 controls the operation of the robot 100 so that the robot 100 holds the microplate 6, to which the specimen has been dispensed, using the claw members 121 and 121 of the hand 120 attached to the arm 103L (or the arm 103R). Then, the controller 300 controls the operation of the robot 100 so that the robot 100 inserts the held microplate 6 into the incubator 7, whereby the contents of the microplate 6 are thus started to be cultured by the incubator 7. Here, starting the culture of the contents of the microplate 6 as a result of the robot 100 inserting the microplate 6 into the incubator 7 corresponds to the robot 100 performing a predetermined operation on the specimen.

Figure 13A:
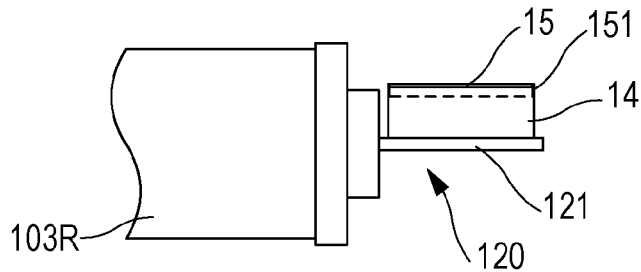
FIGS. 13A to 13D illustrate an operation of a robot.
Figure 13B:
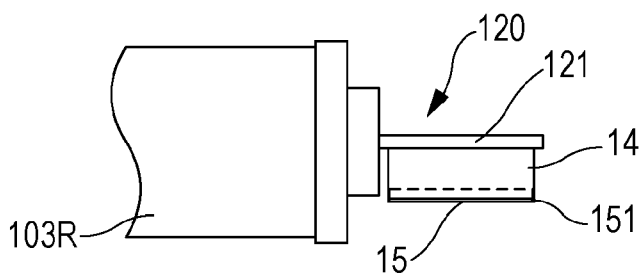
Figure 13C:
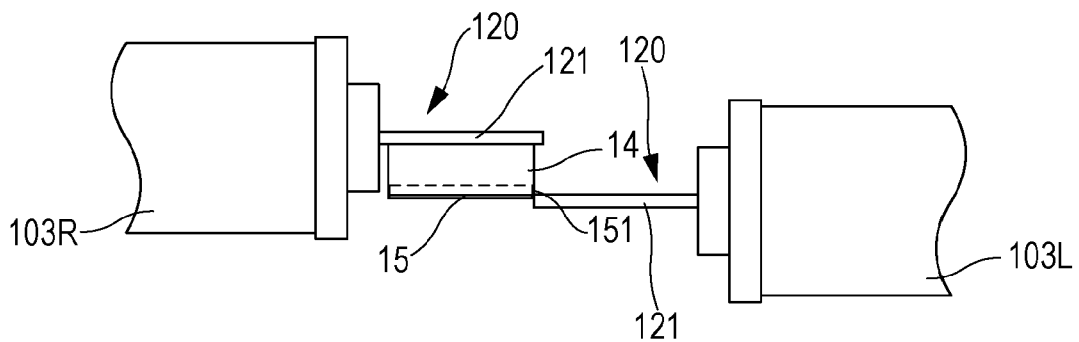
Figure 13D:
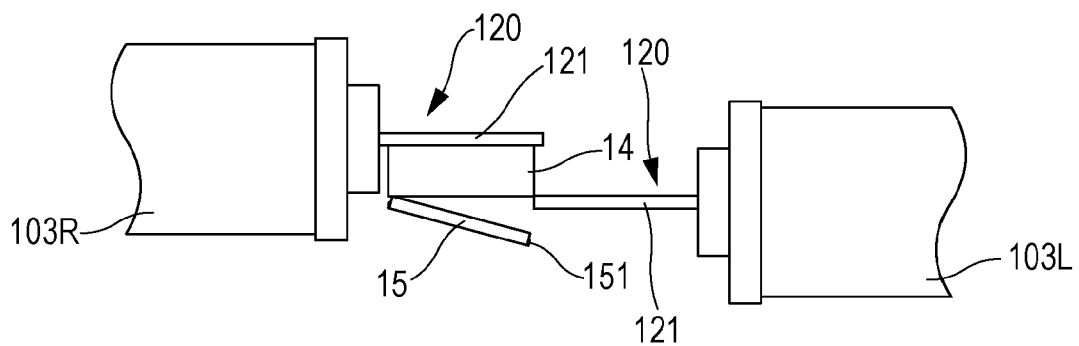

When all the pipette tips 13 on the tip pallet 15 on the tip box 14 held by the holding member 10 thus placed are used up (when the tip pallet 15 is emptied of the pipette tips 13), in Step S100, the controller 300 controls the operation of the robot 100 so that the robot 100 holds the tip box 14 on which the emptied tip pallet 15 is mounted using the claw members 121 and 121 of the hand 120 attached to the arm 103R (or the arm 103L) in such a manner that the emptied tip pallet 15 comes to the upper side (see FIG. 13A). Subsequently, the third operation controlling unit 303 of the controller 300 controls the operation of the robot 100 so that the robot 100 turns the held tip box 14 upside down in such a manner that the emptied tip pallet 15 comes to the lower side (see FIG. 13B). Thereafter, the controller 300 controls the operation of the robot 100 so that the robot 100 operates the hooks 151 of the tip pallet 15 so that the emptied tip pallet 15 is dropped out of the held tip box 14 using the claw members 121 of the hand 120 attached to the arm 103L (see FIGS. 13C and 13D). Thus, the emptied tip pallet 15 is dropped out of the held tip box 14 and thrown into the waste container 12. Thereafter, the controller 300 controls the operation of the robot 100 so that the robot 100 moves the held emptied tip box 14 in such a manner that the tip box 14 is held by the holding member 10 thus placed.

In Step S110, the controller 300 controls the operation of the robot 100 so that the robot 100 holds the holding member 10 thus placed using the claw members 121 and 121 of the hand 120 attached to the arm 103R (or the arm 103L). Then, the controller 300 controls the operation of the robot 100 so that the robot 100 moves the held holding member 10 to a position immediately below the opening 99 (see FIG. 14).

Figure 14:
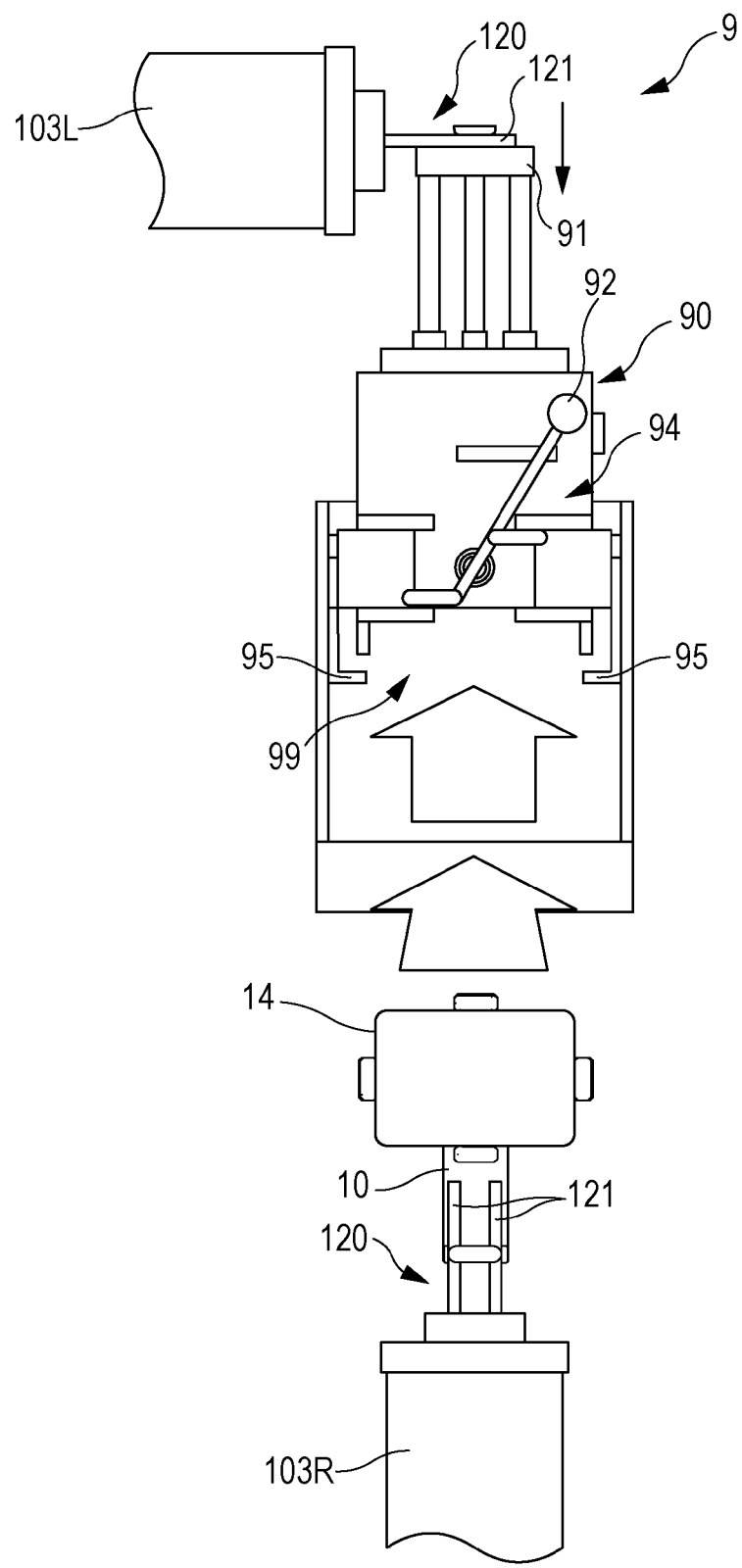
FIG. 14 illustrates an operation of a robot.
Figure 15:
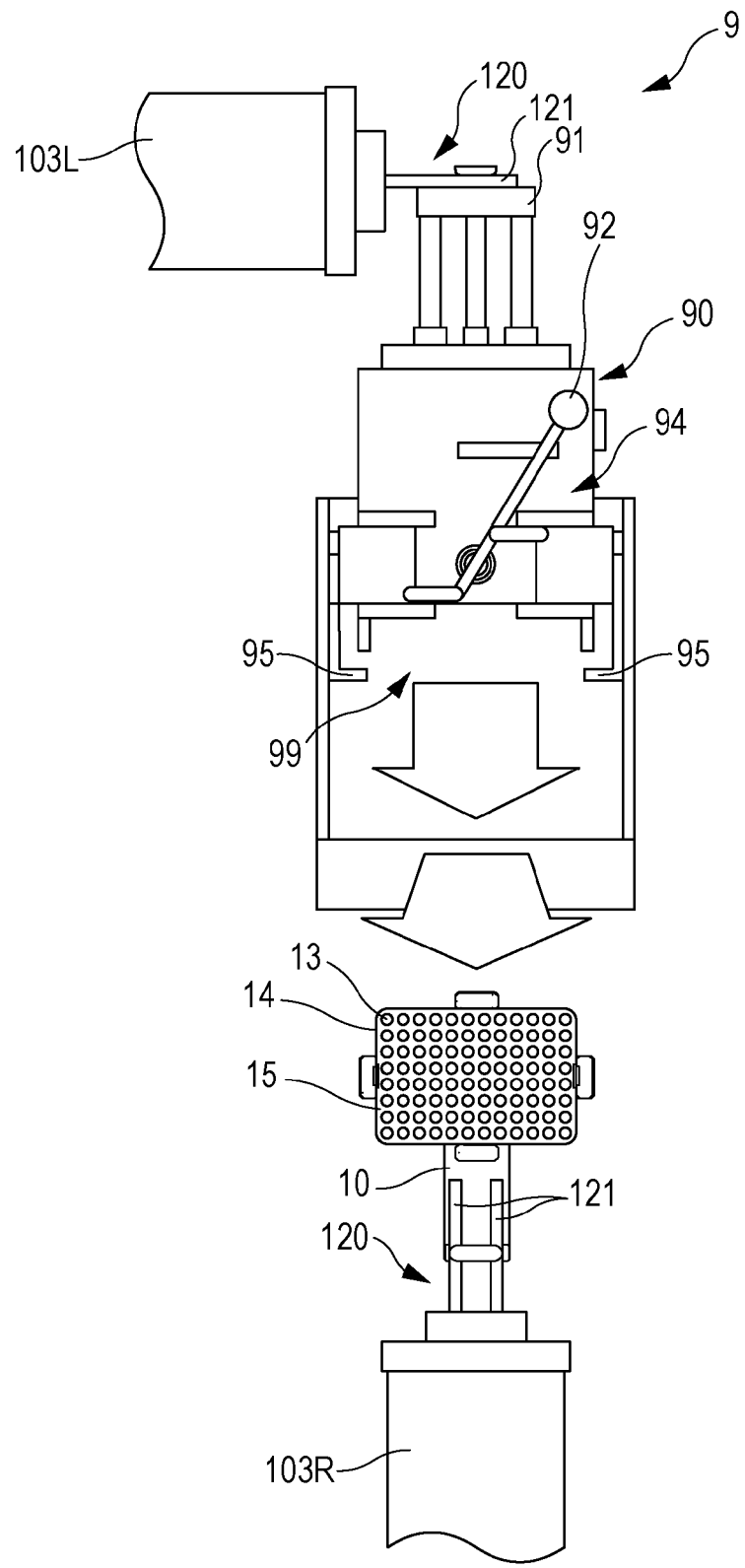
FIG. 15 illustrates an operation of a robot.

In Step S120, the first operation controlling unit 301 of the controller 300 controls the operation of the robot 100 so that the robot 100 slides the slide lever 91 downward into the tip chamber 96 by a predetermined distance so that only one of the tip pallets 15 housed in the tip chamber 96 is pushed out of the tip chamber 96 by the claw members 121 of the hand 120 attached to the arm 103L (or the arm 103R) (see FIG. 14 and FIG. 15). As a result of sliding the slide lever 91 into the tip chamber 96 downward by a predetermined distance, the tip pallets 15 housed in the tip chamber 96 is pushed from above by a predetermined distance and only one of the tip pallets 15 is pushed out of the tip chamber 96. Then, the tip pallet 15 thus pushed out is mounted on the held tip box 14.

In Step S130, the controller 300 controls the operation of the robot 100 so that the robot 100 moves the holding member 10, held by the hand 120 attached to the arm 103R using the claw members 121 and 121 and holding the tip box 14 on which the tip pallet 15 is mounted, from the position immediately below the opening 99 onto the worktable 3 and places the holding member 10 on the worktable 3 (see FIG. 15).

The subsequent procedure is the same as Step S50 to Step S130. When all the tip pallets 15 are removed from the tip chamber 96 (when the tip chamber 96 is emptied of the tip pallets 15), in Step S140, the second operation controlling unit 302 of the controller 300 controls the operation of the robot 100 so that the robot 100 rotates the rotatable lever 92 in the direction of arrow A using the claw members 121 of the hand 120 attached to the arm 103L (or the arm 103R) (see FIG. 11 and FIG. 12). The rotation of the rotatable lever 92 in the direction of arrow A moves the forward/backward moving members 95 and 95 into the opening 99 toward each other to narrow the opening 99.

In Step S150, the first operation controlling unit 301 of the controller 300 controls the operation of the robot 100 so that the robot 100 slides the slide lever 91 upward out of the tip chamber 96 using the claw members 121 of the hand 120 attached to the arm 103L (or the arm 103R). Thereafter, the operator may be informed that the tip chamber 96 is empty in an appropriate manner (by way of sound such as a buzzer).

The above-described operation flow including multiple steps is provided as a mere example. One of the steps or more may be omitted or changed or one step or more may be added to the above-described steps.

Effects Of Embodiments

As described above, the robot system 1 according to some embodiments includes the robot 100, the controller 300, and the tip stocker 9. The tip stocker 9 provides the tip box 14 with the pipette tips 13 attached to and detached from the pipette 8 as a result of the operation of the robot 100. In the case, for example, where a general-purpose product is used as the tip stocker 9 manually operated by humans, the tip stocker 9 can be directly used in the robot system 1. Supplying the tip box 14 with new pipette tips 13 can be automated by using the robot 100. Thus, all the steps related to the dispensing operation including the step of mounting one of the pipette tips 13, arranged on the tip box 14, on the pipette 8 and the step of dispensing the specimen using the pipette 8 can be automated. Consequently, the dispensing operation can be automated while utilizing general-purpose products.

In this embodiment, particularly, the tip stocker 9 includes a movable member 93 that moves in accordance with the operation of the robot 100. The tip stocker 9 is thus operable by moving the movable member 93 with the operation of the robot 100. Consequently, the robot 100 can more reliably operate the tip stocker 9.

In this embodiment, particularly, the tip stocker 9 includes the tip chamber 96 that houses the tip pallets 15 on which the pipette tips 13 are arranged. When the first operation controlling unit 301 of the controller 300 controls the operation of the robot 100 so that the robot 100 slides the slide lever 91 (pushes the slide lever 91 in), the housed tip pallets 15 are pushed out of the tip chamber 96. Thus, the pushed-out tip pallets 15 can be mounted on the tip box 14 and the pipette tips 13 can be efficiently supplied to the tip box 14. When the tip chamber 96 is emptied as a result of the tip pallets 15 being pushed out, the first operation controlling unit 301 controls the operation of the robot 100 so that the robot 100 slides the slide lever 91 (pushes the slide lever 91 back) so that a space for housing new tip pallets 15 is secured in the tip chamber 96.

In this embodiment, particularly, the tip chamber 96 houses multiple tip pallets 15 stacked one on top of the other. When the first operation controlling unit 301 controls the operation of the robot 100 so that the robot 100 slides the slide lever 91 (pushes the slide lever 91 in), the tip pallets 15 are pushed out of the tip chamber 96 one by one. Thus, every time the pipette tips 13 arranged on one tip pallet 15 are used up, a new tip pallet 15 can be sequentially automatically mounted on the tip box 14. Thus, a dispensing process using a large number of pipette tips 13 can be also automated by using the robot 100.

In this embodiment, particularly, the tip stocker 9 includes forward/backward moving members 95 that move into and out of the opening 99 in directions such as to open and close the opening 99 in order to push out the tip pallets 15. The forward/backward moving members 95 are used to hold objects housed in the tip chamber 96 and to release the objects. Specifically, when the tip box 14 on which the tip pallets 15 are mounted is placed in the tip chamber 96, the opening 99 is narrowed by the forward/backward moving members 95 as a result of the second operation controlling unit 302 of the controller 300 controlling the operation of the robot 100 so that the robot 100 rotates the rotatable lever 92 (moves the forward/backward moving members 95 in directions such that the forward/backward moving members 95 close the opening 99). Thus, the housed tip box 14 can be held in the tip chamber 96. At the start of the dispensing process, the opening 99 is opened by the forward/backward moving members 95 as a result of the second operation controlling unit 302 of the controller 300 controlling the operation of the robot 100 so that the robot 100 rotates the rotatable lever 92 (moves the forward/backward moving members 95 in directions such that the forward/backward moving members 95 open the opening 99). Thus, the tip box 14 can be pushed out of the tip chamber 96 while the tip pallet 15 is left in the tip chamber 96. Then, the opening 99 is kept open, so that the tip pallets 15 can be pushed out of the tip chamber 96 and mounted on the tip box 14 at appropriate timing. In this manner, the tip box 14 on which the tip pallets 15 are mounted can be placed in the tip chamber 96 and used. Consequently, general-purpose products can be used as the tip box 14 on which multiple tip pallets 15 are mounted, whereby the purpose of use of the tip stocker 9 can be further widened.

In this embodiment, particularly, the robot 100 can hold the tip box 14 using the ends of the arms 103L and 103R. Moreover, the third operation controlling unit 303 of the controller 300 controls the operation of the robot 100 so that the robot 100 turns the held tip box 14 upside down. The tip pallet 15 can thus be dropped out of the tip box 14, whereby replacement of used tip pallets 15 can be automated.

In this embodiment, particularly, the robot 100 and the tip stocker 9 are housed in the cabinet 2. Thus, the dispensing operation can be performed by the robot 100 inside the cabinet 2, thereby improving the safety. The cabinet 2 includes the door 206 at a position near the tip stocker 9. This positioning of the door 206 facilitates an access of operators to the tip chamber 96 of the tip stocker 9, thereby improving the workability of placing the tip box 14.

In this embodiment, particularly, the fan 22 adjusts air flow inside the internal space 21 of the cabinet 2. Thus, the internal space 21 of the cabinet 2 can be kept at a positive pressure with respect to the outside while the fan 22 produces air flow flowing downward from the ceiling 218 to the floor 217, whereby the internal space 21 of the cabinet 2 can be kept aseptic.

In this embodiment, particularly, the robot 100 includes two separate arms 103L and 103R. Thus, the separate arms 103L and 103R can perform different operations in parallel, whereby each step can be promptly performed. Moreover, a complex operation can be performed using both arms 103L and 103R together. Furthermore, since the two arms 103L and 103R are supported at portions on both sides of the trunk 102, the arms 103L and 103R can perform their operations independently of each other without interfering with each other.

Modified Examples

The embodiment is not limited to the above description and various modifications can be made within the scope not departing from the gist and the technical scope of the disclosure.

Specifically, in the above-described embodiment, the robot 100 holds the tip box 14 using the holding member 10 held with the claw members 121 and 121 of the hand 120 when, for example, the tip pallet 15 is mounted on the tip box 14. However, this is not the only possible way of holding the tip box 14. The tip box 14 may be directly held with the claw members 121 and 121 of the hand 120 without using the holding member 10.

In the above-described embodiment, components such as the robot 100 and the tip stocker 8 are housed in the cabinet 2. However, this is not the only possible configuration. These components do not have to be housed in the cabinet 2.

In the above-described embodiment, each of the arms 103L and 103R of the robot 100 includes seven joints and has one redundant degree of freedom with respect to three translational degrees of freedom and three rotational degrees of freedom. However, the arms are not limited to this configuration and may be any arms that have two joints or more.

In the above-described embodiment, the robot 100 is a dual-arm robot including two arms 103L and 103R. However, the robot is not limited to this and may be any robot that includes at least one arm including multiple joints.

In addition to the above description, methods according to some embodiments and modified examples may be appropriately combined.

Although not exemplified one by one, the above-described embodiment and modified examples may be embodied by being modified in various manners within the scope not departing from the gist of the disclosure.

It should be understood by those skilled in the art that various modifications, combinations, sub-combinations and alterations may occur depending on design requirements and other factors insofar as they are within the scope of the appended claims or the equivalents thereof.

What is claimed is:
1. A robot system, comprising:
a robot including an arm;
a feeder configured to supply a pallet among a plurality of pallets to a tip box, the feeder comprising:
   a chamber in which the plurality of pallets are to be stacked in a vertical direction:
   a slide lever configured to slide into the chamber in the vertical direction so as to push the pallet out of the chamber and supply the pallet to the tip box provided under the plurality of pallets;
   a moving member configured to move into and out of an opening through which the pallet is pushed out of the chamber; and
   a rotatable lever configured to move the moving member into and out of the opening by performing a rotational operation; and a controller configured to control the arm of the robot to slide the slide lever into the chamber in the vertical direction and controls the arm of the robot to rotate the rotatable lever.

2. The robot system according to claim 1,
wherein the robot is configured to hold the box at an end of the arm, and
wherein the controller controls the arm of the robot so that the robot turns the box held at the end of the arm upside down or tilts the box held at the end of the arm.

3. The robot system according to claim 1, further comprising a cabinet that houses the robot and the feeder and that includes an openable-closable door at a portion close to the feeder.

4. The robot system according to claim 3, further comprising an air-flow adjusting device to adjust air flow of an internal space of the cabinet.

5. The robot system according to claim 1,
wherein the robot includes:
    another arm being separate from the arm; and
    a trunk supporting the arm and the another arm at portions on two sides.

* * * * *